United States Patent [19]

Mc Combie

[11] 4,374,844

[45] Feb. 22, 1983

[54] STABLE DERIVATIVES OF (5R,6S,8R)-6-HYDROXYETHYL-2-ETHYL-THIOPENEM-3-CARBOXYLIC ACIDS

[75] Inventor: Stuart W. Mc Combie, West Orange, N.J.

[73] Assignee: Schering Corporation, Kenilworth, N.J.

[21] Appl. No.: 316,627

[22] Filed: Oct. 30, 1981

Related U.S. Application Data

[63] Continuation-in-part of Ser. No. 219,410, Dec. 22, 1980, abandoned, which is a continuation-in-part of Ser. No. 91,610, Nov. 5, 1979, abandoned, which is a continuation-in-part of Ser. No. 62,875, Aug. 1, 1979, abandoned, which is a continuation-in-part of Ser. No. 2,471, Jan. 10, 1979, abandoned.

[30] Foreign Application Priority Data

Jan. 7, 1980 [EP] European Pat. Off. ........ 80810004.4

[51] Int. Cl.$^3$ .................. C07D 499/00; A61K 31/425
[52] U.S. Cl. .............................. 424/270; 260/245.2 R
[58] Field of Search .................. 260/245.2 R; 424/270

[56] References Cited

U.S. PATENT DOCUMENTS 4,260,618 4/1981 Christensen et al. ............... 424/270

FOREIGN PATENT DOCUMENTS 2013674A 10/1979 United Kingdom .

OTHER PUBLICATIONS

Oida et al, Tetrahedron Letters 21 619, (1980).
Mc Combie et al, Tetrahedron Letters 22 3489, (1981).

*Primary Examiner*—Nicholas S. Rizzo
*Attorney, Agent, or Firm*—Gerald S. Rosen; Bruce M. Eisen; Mary S. King

[57] ABSTRACT

Sodium and Potassium (5R,6S,8R)-6-(1-hydroxyethyl)-2-ethylthiopenem-3-carboxylic acid exhibit potent, broad-spectrum antibacterial activity, are orally effective and chemically stable.

10 Claims, No Drawings

STABLE DERIVATIVES OF (5R,6S,8R)-6-HYDROXYETHYL-2-ETHYLTHIOPENEM-3-CARBOXYLIC ACIDS

This application is a continuation-in-part of co-pending U.S. Ser. No. 219,410, filed Dec. 22, 1980 now abandoned, in turn a continuation-in-part of U.S. Ser. No. 091,610, filed Nov. 5, 1979 now abandoned, which is a continuation-in-part of co-pending U.S. Ser. No. 062,875, filed Aug. 1, 1979 now abandoned, which, in turn, is a continuation-in-part of co-pending U.S. Ser. No. 002,471, filed Jan. 10, 1979 now abandoned.

The present invention relates to beta-lactam compositions which exhibit an unusual and highly desirable combination of (1) broad-spectrum antibacterial activity, (2) high potency, (3) efficacy by the oral route of administration and (4) chemical stability.

More particularly, this invention relates to compounds of formula I substantially free of its enantiomer:

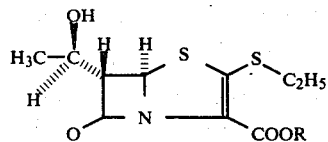

wherein R is sodium or potassium cation. These compounds are:
  sodium (5R,6S,8R)-6-(1-hydroxyethyl)-2-ethylthiopenem-3-carboxylate and
  potassium (5R,6S,8R)-6-(1-hydroxyethyl)-2-ethylthiopenem-3-carboxylate.

Certain processes produce these compounds as their racemic mixtures, i.e., a 5R,6S,8R compound is produced with its enantiomer (mirror image), i.e., a 5S,6R,8S compound, in equal amounts when the starting compound is a racemic mixture. The two enantiomers may be separated by conventional means, e.g., by resolution by fractional crystallizations of optically active salt forms, e.g., the salts derived from optically active amino acids, (−)-brucine, (+)- and (−)-ephedrine. Preferably, the chiral compounds of formula I are produced in their pure enantiomeric form by utilizing optically active intermediates in the synthetic procedure. These optically active intermediates may be produced by conventional resolution or by stereospecific synthesis according to the procedures of E.P.O. Published Application No. 0013662, the disclosure of which is hereby incorporated by reference. A preferred method of preparing the compounds of formula I, specifically described in the examples, utilizes procedures of Adriano Afonso and Frank Hon, U.S. Ser. No. 230,774, filed Feb. 2, 1980 (of common assignee as the instant application), the disclosure of which is incorporated herein by reference.

The designations of absolute spatial configuration are based on X-ray crystal analysis.

The compounds of this invention possess antibacterial activity of both the gram-positive and gram-negative type. Most importantly, they are orally active antibacterial agents which afford effective blood levels at pharmaceutically acceptable dosages. When tested in standardized microbiological assays, the compounds of this invention are active against such gram-positive organisms as *Staphylococcus epidermidis,* and *Bacillus subtilis,* and such gram-negative organisms as *E. coli* and Salmonella at test levels of 0.1 to 100 ug/ml. They are active against organisms which produce penicillanases and cephalosporinases indicating a resistance against this enzyme and, in addition, are inhibitors of beta-lactamases. For instance, sodium (5R,6S,8R)-6-(1-hydroxyethyl)-2-ethylthiopenem-3-carboxylate and the corresponding potassium salt are active against Staphylococcus 76070103 at a test level of 0.5 ug/ml. When tested against *B. subtilis* 1119601 (a beta-lactamase-containing organism), these compounds exhibit activity at 0.06 ug/ml.

Thus, the present invention includes within its scope pharmaceutical compositions comprising an antibacterially effective amount of a penem salt of formula I together with a compatible, pharmaceutically acceptable carrier or coating. In the foregoing compositions, the compounds of this invention can be used alone or in combination with other antibacterial agents.

Also included within this invention is the method of treating a warm-blooded animal having a susceptible bacterial infection which comprises administering to said animal a non-toxic, antibacterially effective amount of a penem salt of formula I. Preferred embodiments concern the oral pharmaceutical compositions and the oral administration of such compositions. A particularly preferred embodiment relates to a pharmaceutical composition which is an oral antibacterial dosage unit comprising a compound of formula I, in an amount sufficient to be orally effective as broad spectrum antibacterial, together with a non-toxic pharmaceutically acceptable carrier. Of these compositions, those which are solid are particularly desirable.

The dosage administered of the penems of this invention is dependent upon the age and weight of the animal species being treated, the exact mode of administration, and the type and severity of bacterial infection being prevented or reduced. Typically, the dosage administered per day will be in the range of 5–125 mg/kg, with 20–80 mg/kg being preferred.

For oral administration, the compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, in the form of creams, or as suppositories.

The compounds of formula I may be utilized in liquid form such as solutions, suspensions and the like for otic and optic use and may also be administered parenterally via intramuscular injection.

The preferred compositions of this invention relate to oral dosage forms of the preferred compounds of this invention, i.e. compounds of formula I wherein R is a sodium or potassium cation. These oral dosage forms are characterized by an unusual combination of high potency, broad antibacterial spectrum and efficacy via the oral route of administration and chemical stability.

Penems have previously been identified as exhibiting interesting antibacterial activity. A number of research teams investigated various substituted penems with hope of finding species having a broad antibacterial spectrum, high potency and oral efficacy. See, for example, Merck E.P.O. No. 2,210 published June 13, 1979, and Ciba-Geigy E.P.O. No. 31,960 published Sept. 19, 1979. However, as noted in the article "New β-lactams being studied as antibiotics" Chemical and Engineering News, pages 19 (Nov. 5, 1979), the penems studied to date did not seem to be suitable for oral dosage forms since they were too rapidly excreted. The narrow subclass of penems of this invention, on the other hand, exhibit broad spectrum antibacterial activity, high potency and efficacy by the oral route of administration. Thus, the compounds of this invention, possess the desirable antibacterial properties of the so-called third generation penicillins and cephalosporins but, in contradistinction to them, are orally effective. Thus, the penem salts of this invention represent a major advance in antibacterial therapy.

While we do not wish to be limited by our theory as to why the compositions of this invention are orally effective, we believe it is due in part to the high level of binding between the subject penem and protein in the blood. This protein binding seems to offset the undesirable rapid excretion property of penems in general.

In addition to the foregoing, the penem sodium and potassium salts of formula I are advantageously and surprisingly more stable in the presence of moisture than are the corresponding acid (i.e. the compound of formula I wherein R is hydrogen) and the corresponding conventional metabolisable esters, e.g. the phthalidyl or pivaloyloxymethyl esters (i.e. compounds of formula I wherein R is phthalidyl or pivaloyloxymethyl) or other pharmaceutically acceptable salts such as the calcium and aluminum salts (i.e. compounds of formula I wherein R is calcium or aluminum. The unexpected greater stability of the sodium and potassium salts of this invention renders the claimed compounds and pharmaceutical compositions thereof unique and greatly superior as clinically suitable antibacterial agents than the corresponding acid, or metabolisable esters or other salts.

Of the compositions of this invention, the most preferred is an oral solid dosage unit comprising sodium (5R,6S,8R)-6-(1-hydroxyethyl)2-ethylthiopenem-3-carboxylate or the corresponding potassium salt in an amount sufficient to be orally effective as a broad spectrum antibacterial, together with a non-toxic pharmaceutically acceptable carrier.

The compounds of this invention are preparable by a reaction sequence starting with 4-ethylthioazetidin-2-one (preparable as described in *Liebigs Ann. Chem.,* 1974 539–560) via procedures described in the Preparations and Examples of this application and in the hereinabove identified parent U.S. applications as well as in the corresponding Schering E.P.O. published application No. 13,662, all of which are incorporated by reference.

PREPARATION A

Allyl Oxalyl Chloride

Allyl alcohol (11.6 g.) is added dropwise with stirring to a cold (0° C.) solution of oxalyl chloride (25.4 g.) in dry ether (50 ml.) while maintaining the temperature of the reaction mixture during the addition at 10°–12° C. The reaction mixture is then stirred overnight followed by removal of the solvent in a rotary evaporator. The resultant residue is distilled to yield allyl oxalyl chloride as a colorless liquid (16 g.), b.p. 68°–70° C./44 mm.

EXAMPLE 1

ALLYL (5R,6S,8R)-6-(1-TRICHLOROETHOXYCARBONYLOXYETHYL)-2-ETHYLTHIOPENEM-3-CARBOXYLATE

To a solution of (3S,4R,5R)-3-(trichloroethoxycarbonyloxyethyl)-4-[(ethylthio)-carbonothioylthio]-azetidine-2-one (0.628 g.) in methylene chloride (6 ml.) cooled to 10° C., add, with stirring, calcium carbonate (0.6 g.) followed by allyloxalyl chloride (0.263 g., 1.2 eq.). Add dropwise a solution of di-isopropylethylamine (0.32 ml., 1.2 eq.) in methylene chloride (1 ml.), during 5 minutes while maintaining the temperature at 10°–15° C. After TLC shows no starting compound (15 mins.), transfer the mixture to a separatory funnel using ethanol-free chloroform. Wash twice with ice-water, filter to remove calcium carbonate, dry over anhydrous sodium sulfate, and transfer to a 100 ml. 3-neck flask. Adjust the volume of the solution to approximately 50 ml. with chloroform and heat at reflux temperature while adding a solution of triethylphosphite (0.6 ml., 2 eq.) in chloroform (20 ml.) over a 3 hour period. Reflux the mixture for an additional 18 hours, evaporate and chromatograph on 14 g silica gel, eluting with 25% ether-hexane, and evaporate the combined like elutes to obtain a residue (420 mg.) comprising the title compound (58% yield). Purify by crystallization from ether-hexane to obtain the compound in crystalline form. Yield 300 mg. (46% theory).

EXAMPLE 2

ALLYL (5R,6S,8R)-6-(1-HYDROXYETHYL)-2-ETHYLTHIOPENEM-3-CARBOXYLATE

To a solution of 1.18 g allyl (5R,6S,8R)-6-[1-trichloroethoxycarbonyloxyethyl]-2-ethylthiopenem-3-carboxylate in 9.0 ml tetrahydrofuran under nitrogen is added 3 ml acetic acid and 500 mg activated zinc powder. The reaction is stirred for 2½ hours during which time additional 400 mg zinc metal is added in two portions. The reaction is followed by thin layer chromatography eluting with 5% ethyl acetate/toluene. The reaction mixture is then filtered and 250 ml methylene chloride added. After washing twice with water, 3 times with cold 3% sodium bicarbonate solution and twice with brine solution, the solution is dried over anhydrous sodium sulfate. Removal of the solvents under vacuum affords 720 mg allyl (5R,6S,8R)-6-(2-hydroxyethyl)-2-ethylthiopenem-3-carboxylate.

EXAMPLE 3

POTASSIUM (5R,6S,8R)-6-(1-HYDROXYETHYL-2-ETHYLTHIOPENEM-3-CARBOXYLATE

To a solution of 700 mg allyl (5R,6S,8R)-6-(1-hydroxyethyl-2-ethylthiopenem-3-carboxylate in 4 ml methylene chloride and 8 ml ethyl acetate under nitrogen is added 46.6 mg triphenylphosphine. To this is added 4.86 ml 0.5 molar potassium 2-ethylhexanoate in ethyl acetate. Then, 51.1 mg tetrakis(triphenylphosphine)palladium is added and the solution is stirred for 15 minutes. An additional 100 mg triphenylphosphine and 25 mg tetrakis(triphenylphosphine)-palladium is added, followed by 10 ml ethyl ether. After stirring until thin layer, chromatography indicates the absence of starting penem ester, the solution is extracted with water (2×25 ml.). The combined aqueous solutions are extracted with ethyl acetate (2×20 ml.), treated with a stream of nitrogen to remove dissolved organic solvents, and finally lyorphilized to give the title compound.

Alternatively, after the additional triphenylphosphine, tetrakis(triphenylphosphine)palladium and ethyl ether are added, the product slowly precipitates and after 1 hour the solution is filtered and washed with ethyl acetate and ethyl ether, to afford 450 mg potassium (5R,6S,8R)-6-(1-hydroxyethyl)-2-ethylthiopenem-3-carboxylate. To the mother liquor is added 20 ml ethyl ether. After refrigeration overnight, a second crop of crystals is filtered to yield an additional 90 mg of the potassium salt.

NMR: $=1.25$–$1.49$, 6H; $=2.76$–$3.14$, 2H; $=3.85$–$3.94$, 1H; $=4.12$–$4.37$, 1H; $=5.65$–$5.67$, 1H, d; ($D_2O$)

Rotation: $\alpha/_D = -145.2°$

EXAMPLE 4

SODIUM (5R,6S,8R)-6-(1-HYDROXYETHYL)-2-ETHYLTHIOPENEM-3-CARBOXYLATE

In the procedure of Example 3, substitute an equivalent amount of sodium -2-ethylhexanoate for potassium 2-ethylhexanoate to obtain sodium (5R,6S,8R) 6-(1-hydroxyethyl)-2-ethylthiopenem-3-carboxylate having the same NMR and Rotation values as the corresponding potassium salt of Example 3.

The following formulations are to exemplify some of the dosage forms in which the antibacterial agents of this invention may be employed. In each, the active ingredient is designated by the term "Drug" which is meant to indicate one of the following compounds:

sodium (5R,6S,8R)-6-(1-hydroxyethyl)-2-ethylthiopenem-3-carboxylate, potassium (5R,6S,8R)-6-(1-hydroxyethyl)-2-ethylthiopenem-3-carboxylate.

EXAMPLE 5

Injection Formulation

Per vial: sodium or potassium (5R,6S,8R)-6-(1-hydroxyethyl)-2-ethylthiopenem-3-carboxylate (Sterile powder). Exemplary unit dosages may be 125 mg., 250 mg., 500 mg., 1 gm. and 2 gms. Add sterile water for injection U.S.P. or bacteriostatic water for injection U.S.P., for reconstitution.

EXAMPLE 6

| Capsule Formulation | | | |
|---|---|---|---|
| Item No. | Ingredient | mg/capsule | mg/capsule |
| 1 | Drug | 250 | 500 |
| 2 | Microcrystalline Cellulose | 30 | 60 |
| 3 | Corn Starch, Dried | 15 | 30 |
| 4 | Silica Gel | 4.5 | 9 |
| 5 | Magnesium Stearate | 0.5 | 1 |
| | | 300.0 mg | 600 mg |

Method

Mix Item Nos. 1, 2, 3 and 4 in a suitable mixer for 10–15 minutes. Add Item No. 5 and mix for 1–3 minutes. Fill the above mixture in two-piece hard gelatin capsules of required size.

Alternatively, mix Item Nos. 1, 2, 3 and 4 in a suitable mixer for 10–15 minutes. Add half the amount of Item No. 5, mix for 1–3 minutes. Pass the mixture through a suitable compactor. Pass the compacted mixture through a suitable mill equipped with 16 mesh screen. Remix and add the remainder amount of Item No. 5. Mix for 1–3 minutes. Fill the above mixture in two-piece hard gelatin capsules of required size.

EXAMPLE 7

| Tablet Formulation | | | |
|---|---|---|---|
| Item No. | Ingredient | mg/tablet | mg/tablet |
| 1 | Drug | 250 | 500 |
| 2 | Microcrystalline Cellulose | 100 | 200 |
| 3 | Corn Starch, Dried | 40 | 80 |
| 4 | Silica Gel | 6 | 12 |
| 5 | Magnesium Stearate | 4 | 8 |
| | | 400 mg | 800 mg |

Method

Mix Item Nos. 1, 3 and half the amount of Item No. 4 in a suitable mixer for 10–15 minutes. Add half the amount of Item No. 5 and mix for 1–3 minutes. Pass the mixture through a suitable compactor. (Alternatively, slug the mixture on a rotary tablet machine equipped with 1" flat bevelled punches). Mill the compacted material or the slugs using a suitable milling machine equipped with 16 mesh screen. Remix. Add Item No. 2 and the remainder amount of Item No. 4. Mix for 10–15 minutes. Add the balance of Item No. 5 and mix for 1–3 minutes. Compress the mixture into the tablets of required shape and size on a rotary tablet machine. The tablets may be coated using standard coating procedures.

EXAMPLE 8

| Topical Formulation | | |
|---|---|---|
| Item No. | Ingredient | mg/g |
| 1 | Drug | 25 |
| 2 | Ethyl Alcohol | 400 |
| 3 | Hydroxypropyl Cellulose | 15 |
| 4 | Polyethylene Glycol 400 | 560 |

Mix Item Nos. 1, 2 and 4 in a suitable mixer. Stir vigorously and charge Item No. 3. Maintain stirring until uniformity is achieved.

EXAMPLE 9

| Oral Powder for Reconstitution (I) Part A (Powder Formulation) | | |
|---|---|---|
| Item No. | Ingredient | mg/g |
| 1 | Drug | 46.3 |
| 2 | Flavor(s) | q.s. |
| 3 | Colorant | q.s. |
| 4 | Preservative | q.s. |
| 5 | Buffer Agents | q.s. |
| 6 | Sugar | q.s. |
| | To make | 1.0 g |

Mix Item Nos. 1, 2, 3, 4 and 5 thoroughly. Charge Item No. 6 and mix until uniformity is achieved.

PART B (RECONSTITUTION)

Charge 54 g of above formulated powder into a proper container and add enough water to make up 100 ml. Shake well after the addition of water. Each 5 ml (1 teaspoonful) will then contain drug equivalent to 125 mg.

EXAMPLE 10

| Item No. | Oral Liquid Ingredient | mg/ml |
|---|---|---|
| 1 | Drug | 25.0 |
| 2 | Sweetner | q.s. |
| 3 | Flavor | q.s. |
| 4 | Colorant | q.s. |
| 5 | Vegetable Oil | q.s. |
| | To make | 1.0 ml |

Charge 90% of Item No. 5 needed into a suitable container. Charge Item Nos. 1, 2, 3 and 4 and mix well. Bring to the final volume by the reserved Item No. 5.

I claim:

1. Sodium (5R,6S,8R)-6-(1-hydroxyethyl)-2-ethylthiopenem-3-carboxylate substantially free from its enantiomer.

2. Potassium (5R,6S,8R)-6-(1-hydroxyethyl)-2-ethylthiopenem-3-carboxylate substantially free from its enantiomer.

3. A pharmaceutical composition comprising an antibacterially effective amount of a compound of claim 1 together with a non-toxic pharmaceutically acceptable carrier.

4. A pharmaceutical composition comprising an antibacterially effective amount of a compound of claim 2 together with a non-toxic pharmaceutically acceptable carrier.

5. A composition of claim 3 which is an oral antibacterial dosage unit comprising a compound of claim 1 in an amount sufficient to be orally effective as a broad spectrum antibacterial, together with a non-toxic pharmaceutically acceptable carrier.

6. A composition of claim 4 which is an oral antibacterial dosage unit comprising a compound of claim 1 in an amount sufficient to be orally effective as a broad spectrum antibacterial, together with a non-toxic pharmaceutically acceptable carrier.

7. An oral dosage unit according to claims 5 or 6 which is solid.

8. A method of effectively treating a warm-blooded animal having a susceptible bacterial infection which comprises administering to said animal a non-toxic, antibacterially effective amount of a composition of claim 3.

9. A method of effectively treating a warm-blooded animal having a susceptible bacterial infection which comprises administering to said animal a non-toxic, antibacterially effective amount of a composition of claim 4.

10. A method according to claims 8 or 9 wherein the composition is administered orally.

* * * * *